United States Patent [19]
Rohr

[11] Patent Number: 6,143,232
[45] Date of Patent: Nov. 7, 2000

[54] METHOD OF MANUFACTURING AN ARTICULATING BEARING SURFACE FOR AN ORTHOPAEDIC IMPLANT

[75] Inventor: William Rohr, Marshfield, Mass.

[73] Assignee: Bristol-Meyers Squibb Company, New York, N.Y.

[21] Appl. No.: 09/361,210

[22] Filed: Jul. 29, 1999

[51] Int. Cl.[7] .......................... B29B 13/08; B29C 43/02
[52] U.S. Cl. .................... 264/460; 264/126; 264/320; 264/461; 264/462; 264/463
[58] Field of Search .................. 264/126, 320, 264/460, 461, 462, 463, 485, 488, 492, 494

[56] References Cited

U.S. PATENT DOCUMENTS

| | | |
|---|---|---|
| 3,297,641 | 1/1967 | Werber et al. |
| 3,352,818 | 11/1967 | Meyer et al. |
| 3,758,273 | 9/1973 | Johnston et al. |
| 5,037,928 | 8/1991 | Li et al. |
| 5,160,464 | 11/1992 | Ward et al. |
| 5,414,049 | 5/1995 | Sun et al. |
| 5,449,745 | 9/1995 | Sun et al. |
| 5,466,530 | 11/1995 | England et al. |
| 5,543,471 | 8/1996 | Sun et al. |
| 5,879,400 | 3/1999 | Merrill et al. |

FOREIGN PATENT DOCUMENTS

| | | |
|---|---|---|
| 722973 A1 | 7/1996 | European Pat. Off. |
| WO 98/01085 | 1/1998 | WIPO |

OTHER PUBLICATIONS

*Super Low Wear Cross–Linked UHMWPE by Heavy High–Dose Gamma Radiation* Oonishi, H., Kuno, M., Idada, Y., Fujisawa, A., and Masuda, S. 1996 WPOA 2$^{nd}$ Congress of Hip Section.

*Journal of Polymer Science, Part B, Polymer Letters*, Turner D. T. vol. 1, No., Feb. 1963, pp. 101–103.

*The Improvement of Polyethylene Prostheses Through Radiation Crosslinking* T.A. du Plessis, C. J. Grobbelaar, and F. Marais Radiat. Phys. Chem. 1977, vol. 9, pp. 647–652.

*The Friction and Wear Behavior of Irradiated Very High Lecular Weight Polyethylene* C. Shen and J.H. Dumbleton Wear, (1974) pp. 349–364.

*Crystalline and Supermolecular Structures in Linear Polyethylene Irradiated with Fast Electrons* G. Gielenz and B. J. Jungnickel Colloid & Polymer Science 260, pp. 742–753 (1982).

*Improved Mechanical Behaviour in Ultra–High Modulus Polyethylenes by Controlled Cross–Linking* D. W. Woods, W. K. Busfield and I.M. Ward Plastics and Rubber Processing and Applications 5 (1985) pp. 157–164.

*Irradiation of Ultrahigh–Molecular–Weight Polyethylene* A. Shinde and R. Salovey Journal of Polymer Science: Polymer Physics Edition, vol. 23, 1681–1689 (1985).

*Ionizing Irradiation for Sterilization and Modification of High Molecular Weight Polyethylenes* Robert M. Streicher Plastics and Rubber Processing and Applications vol. 10, No. 4, 1988.

(List continued on next page.)

*Primary Examiner*—Leo B. Tentoni
*Attorney, Agent, or Firm*—Carl R. Reeves

[57] ABSTRACT

A method of manufacturing an articulating bearing surface for use in an orthopaedic implant uses a supply of ultra-high molecular weight polyethylene particles which are irradiated with sufficient radiation energy to crosslink at least a portion of the ultra-high molecular weight polyethylene. The irradiated particles are then formed into an orthopaedic bearing surface.

12 Claims, 3 Drawing Sheets

OTHER PUBLICATIONS

*Influence of Ionizing Irradiation in Air and Nitrogen for Sterilization of Surgical Grade Polyethylene for Implants* R. M. Streicher Radiat. Phys. Chem, vol. 31, Nos. 4–6, pp. 693–698, 1988.

*Improvement of Polyethylene by Irradiation in Artificial Joints* H. Oonishi, Y. Takayama, and E. Tsuri Radiat. Phys. Chem. vol. 39, No. 6, pp. 495–504, 1992.

*The Radiation Chemistry of Polyethylene. IX. Temperature Coefficient of Cross–Linking and Other Effects* H. Y. Kang, O. Saito, and M. Dole Journal of the American Chemical Society, 89:9, Apr. 26, 1967.

*The Radiation Improvement of Polyethylene Prostheses, A Preliminary Study* C. J. Grobbelaar, T. A. Du Plessis, F. Marais The Journal of Bone and Joint Surgery 60–B, No. 3, Aug. 1978, pp. 370–374.

*The Effects of Radiation Sterilization on the Properties of Ultrahigh Molecular Weight Polyethylene* H. J. Nusbaum and R. M. Rose Journal of Biomedical Materials Research, vol. 13, pp. 557–576 (1979).

*Radiation Sterilization and the Wear Rate of Polyethylene* R. M. Rose, E. V. Goldfarb, E. Ellis, and A. N. Crugnola Journal of Orthopaedic Research, pp. 393–400, 1984 Orthopaedic Research Society.

*Cross–Linking of Ultra–High Molecular Weight Polyethylene in the melt by means of Electron Beam Irradiation* D. J. Dijkstra, W. Hoogsteen, and A. J. Pennings Polymer, 1989, vol. 30, May.

*Effect of γ Irradiation on the Friction and Wear of Ultrahigh Molecular Weight Polyethylene* William R. Jones, Jr., and William F. Hady, Wear, 70 (1981) 77–92.

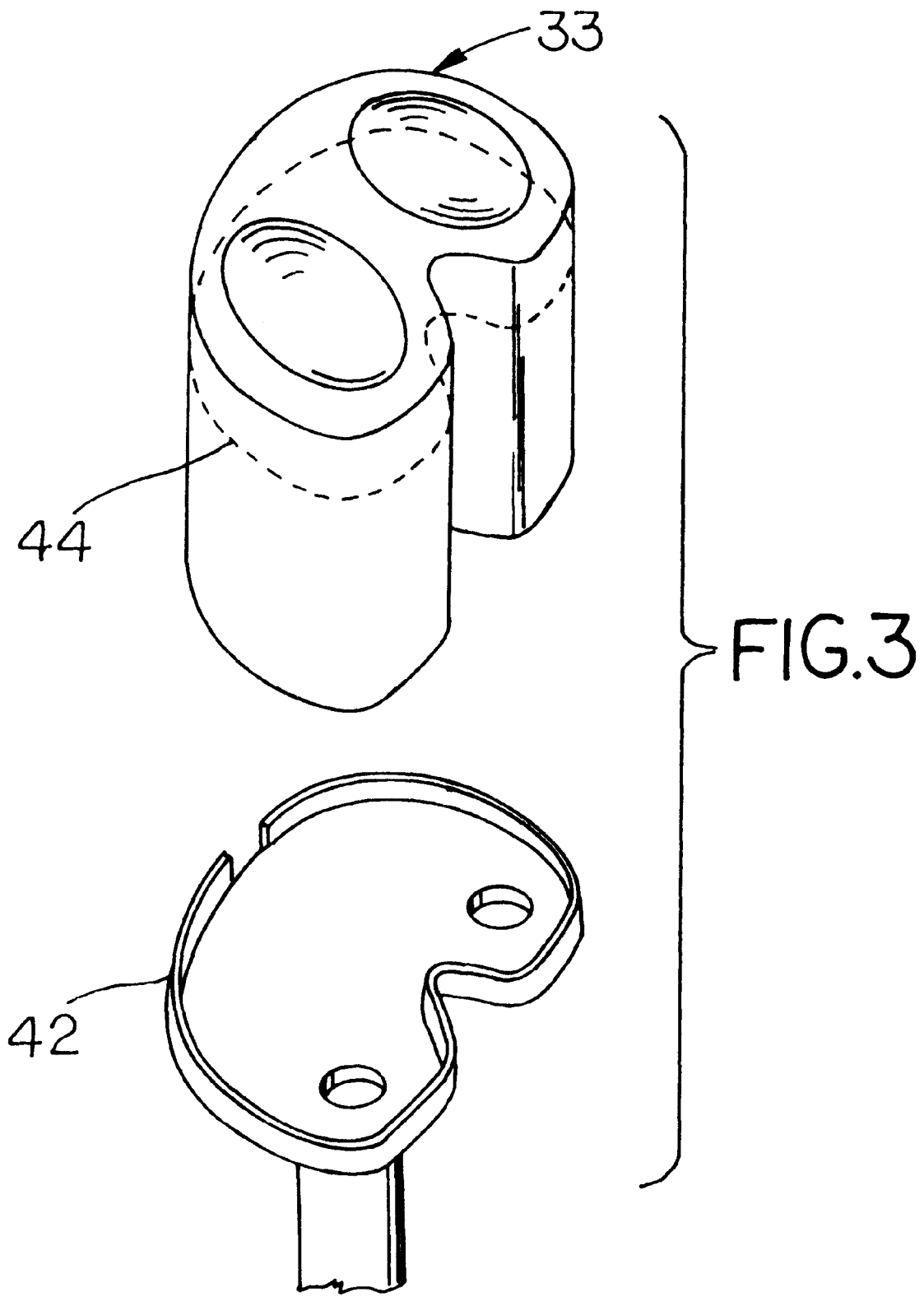

METHOD OF MANUFACTURING AN ARTICULATING BEARING SURFACE FOR AN ORTHOPAEDIC IMPLANT

BACKGROUND OF THE INVENTION

1. Field of the Invention

The present invention relates to orthopaedic implants, and, more particularly, to articulating bearing surfaces for orthopaedic implants.

2. Description of the Related Art

Orthopaedic implants used to reconstruct a joint of a patient typically include two implant halves with each implant half defining an articulating bearing surface. For example, an orthopaedic knee implant includes a proximal component which is placed within the femur and a distal component which is placed within the tibia. The proximal component typically includes a metallic articulating bearing surface which pivots on a non-metallic articulating bearing surface defined by the tibial knee component. The non-metallic bearing surface may be formed from a block of ultra-high molecular weight polyethylene (UHMWPE) which is machined to define the articulating bearing surface. The non-metallic bearing surface is attached to and carried by a tibial tray, which in turn is affixed to a stem inserted within the intramedullary canal (IM) of the tibia.

It is known to irradiate a bearing surface constructed from UHMWPE to crosslink the plastic material and improve the wear properties. The bearing surface is formed to a final shape and the entire bearing surface is irradiated. The penetration of the radiation depends upon factors such as the radiation energy, shape of the bearing surface, etc.

SUMMARY OF THE INVENTION

The present invention provides a method of manufacturing an articulating bearing surface for use in an orthopaedic implant, wherein UHMWPE particles such as powder or flakes are irradiated prior to being shaped into the bearing surface.

The invention comprises, in one form thereof, a method of manufacturing an articulating bearing surface for use in an orthopaedic implant. A supply of UHMWPE particles are irradiated with sufficient radiation energy to crosslink at least a portion of the UHMWPE. The irradiated particles are then formed into an orthopaedic bearing surface.

An advantage of the present invention is that irradiation of the UHMWPE can be better controlled.

Another advantage is that crosslinking of the UHMWPE is accomplished without consideration of the geometric configuration of the articulating bearing surface.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 3 is a perspective view of an articulating bearing surface formed using the apparatus of FIG. 1 and the compression mold of FIG. 2, shown in association with a tibial tray.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
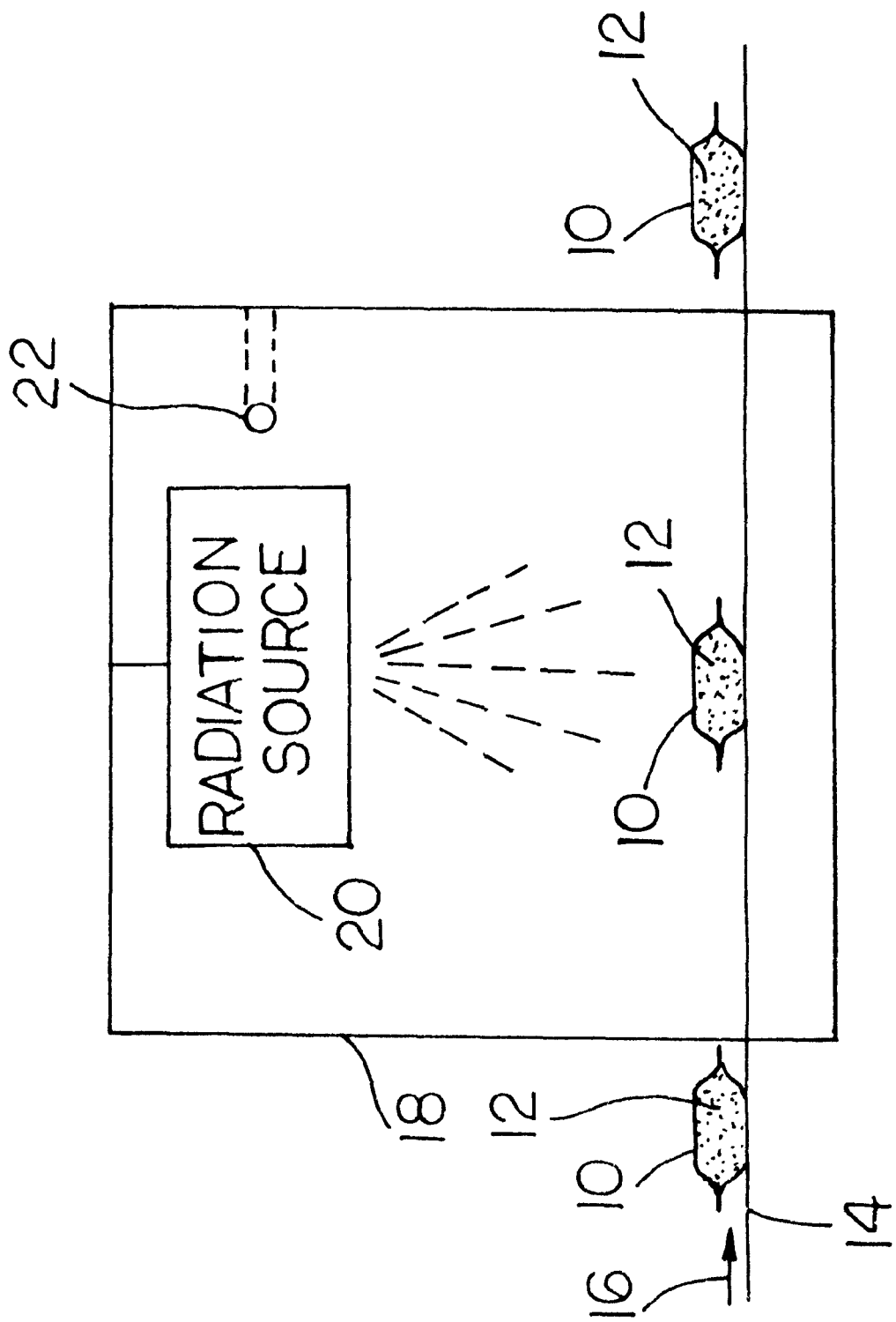
FIG. 1 is a schematic view of an apparatus utilized in an embodiment of the method of the present invention for crosslinking UHMWPE used to make an articulating bearing surface.
Figure 2:
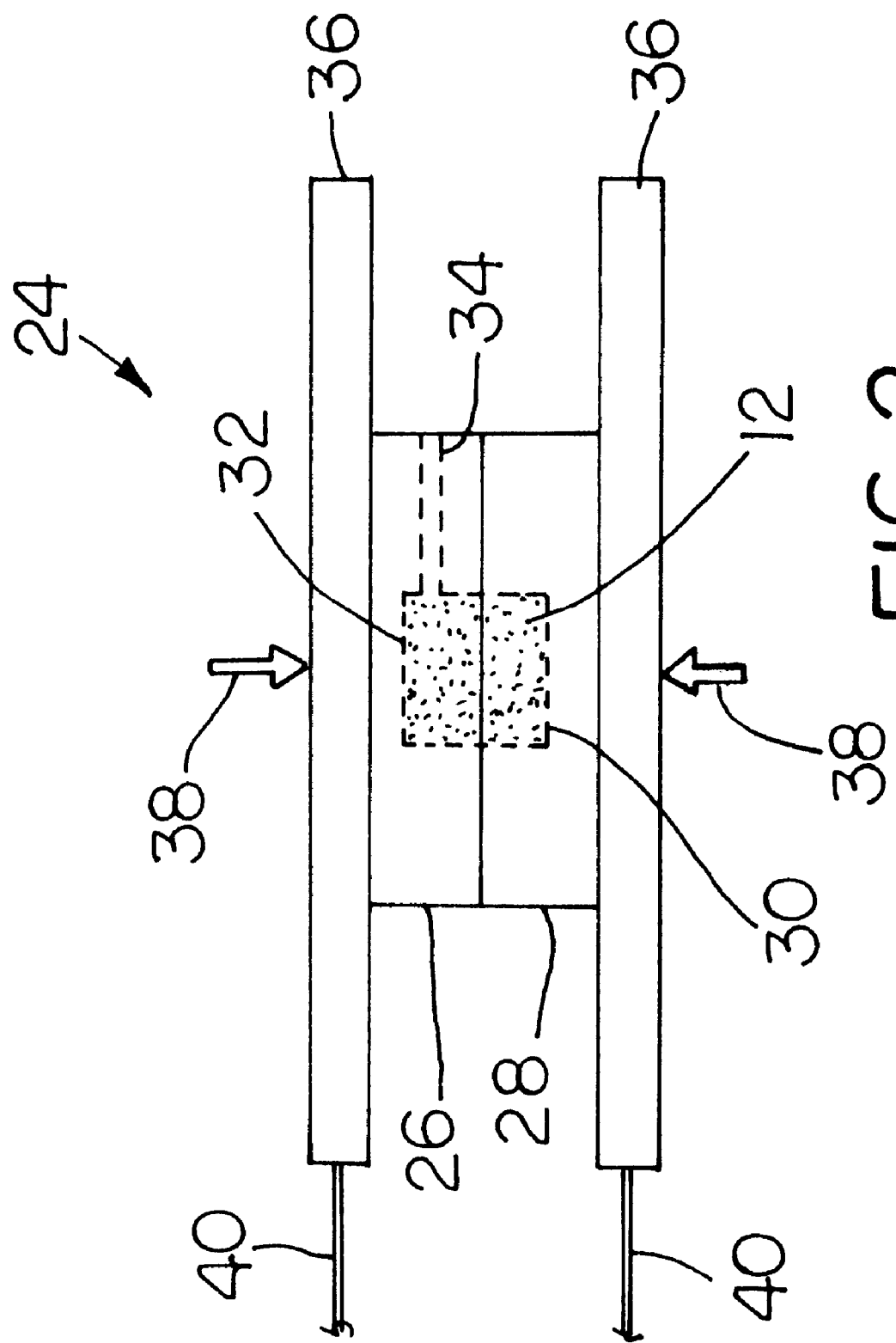
FIG. 2 is a plan view of a compression mold and heated platen assembly used to form the crosslinked UHMWPE into an articulating bearing surface.

Referring now to the drawings, an embodiment of the method of the present invention for forming an orthopaedic articulating bearing surface of the present invention will be described.

Packets 10 include a supply of UHMWPE particles 12 such as powder and/or flakes. Packets 10 are formed from a radiolucent material such as plastic which allows radiation energy to impinge upon particles 12 therein. Packets 12 may be sealed using any suitable technique, such as heat or ultrasonic welding. Particles 12 may have a size and shape which is suitable for any orthopaedic application utilizing an articulating bearing surface. For example, particles 12 may have a size which is between approximately 50 and 200 microns.

Packets 10 are preferably sized to hold an amount of UHMWPE particles 12 which is sufficient to form a desired articulating bearing surface. That is, each packet 10 preferably holds an amount corresponding to a single charge of a compression mold, as will be described hereinafter.

Packets 10 are carried by a conveyor belt 14 which moves in a traveling direction 16. Each packet 10 is carried to an interior of an irradiation apparatus 18, including a radiation source 20 and a gas port 22. Gas port 22 is used for reducing an amount of oxygen which is present within irradiating apparatus 18 during irradiation of packets 10 with radiation source 20. For example, gas port 22 may be used for transporting an inert gas such as nitrogen or argon into an interior of irradiating apparatus 18. A reduced oxygen atmosphere within irradiating apparatus 18 inhibits oxidation of particles 12 within packets 10. Alternatively, gas port 22 may be utilized to draw a vacuum on the interior of irradiating apparatus 18 to reduce the oxygen atmosphere therein. If the material from which packet 10 is constructed is not gas permeable, it may also be possible to load the interior of each packet 10 with an inert gas around particles 12, thereby eliminating the need for reducing the oxygen atmosphere within irradiating apparatus 18.

Radiation source 20 transmits radiation energy which impinges upon particles 12 within packet 10 disposed within irradiating apparatus 18. Radiation source 20 irradiates particles 12 within packet 10 with a sufficient amount of radiation energy to crosslink at least a portion of the UHMWPE from which particles 12 are constructed. Dependent upon the amount of radiation energy used during the crosslinking process, the penetration depth of the radiation energy into particles 12 within packet 10 varies. Preferably enough radiation energy is used to crosslink substantially all of particles 12 within packet 10. The radiation energy preferably is in the form of gamma ray or X-ray radiation, but may also be in the form of ultra-violet radiation, or a radiation beam such as a neutron particle beam, proton particle beam or electron particle beam. In the embodiment shown, the UHMWPE particles 12 within packet 10 are crosslinked using a 10 MeV electron beam providing a total radiation dose level of between approximately 25 and 500 KGy preferably between 100 and 250 KGy, and more preferably between 140 and 180 KGy.

After a packet 10 disposed within irradiating apparatus 18 is crosslinked using radiation energy from radiation source 20, conveyor belt 14 moves the crosslinked packet 10 out of irradiating apparatus 18 and another packet 10 is moved into irradiating apparatus 18 for crosslinking. The crosslinking of the UHMWPE particles 12 within each packet 10 therefore occurs in a batch manner. It may also be possible to crosslink UHMWPE particles 12 in a continuous manner if particles 12 are not disposed within packets, but rather are carried in a continuous manner in a thin layer on conveyor belt 14 through irradiating apparatus 18. The radiation energy and the travel speed of conveyor belt 14 can be easily matched to provide effective crosslinking of the UHMWPE particles 12 if a continuous process is utilized.

After UHMWPE particles 12 are crosslinked using radiation energy, the particles 12 are molded to form an articular surface. The particles 12 may be emptied from the packets 10 or molded while still in the packets. The particles, or particles and packets, are placed within a compression mold 24 having two mold halves 26 and 28 which define a mold cavity 30 therebetween. The portion of mold cavity 30 defined by mold half 26 includes a complimentary articulating bearing surface 33 against which particles 12 are pressed to define an articulating bearing surface 33 (FIG. 3). A gas port 34 is used to reduce the amount of oxygen within mold cavity 30. Reducing the amount of oxygen within mold cavity 30 during the manufacturing process inhibits oxidation of the UHMWPE particles 12. The oxygen within mold cavity 30 may be reduced by applying a vacuum pressure to mold cavity 30 using a vacuum source (not shown) attached to gas port 34 disposed in communication with mold cavity 30. Alternatively, an inert gas such as nitrogen or argon may be introduced into mold cavity 30 through gas port 34.

Mold halves 26 and 28 are assembled together and placed between platens 36 which provide the dual functionality of pressing mold halves 26 and 28 together (indicated by lines 38), as well as heating mold halves 26 and 28 through heat transfer primarily via conduction. Each platen 36 includes an integral heater (not shown) which is connected to a source of electrical power, such as through electrical conductors 40.

Particles 12 are simultaneously pressed together and heated above the melting point of the UHMWPE so that a net shaped articulating bearing surface 33 is formed. Heating the UHMWPE above its melting point allows free radicals in the UHMWPE formed during the crosslinking step to react with other free radicals in the UHMWPE, thereby forming a stable bond. The amount of time required during the forming process may take from a few minutes to several hours, depending upon whether the temperature of the UHMWPE is raised substantially above the melting point thereof, or is maintained at or slightly below the melting point thereof.

After the net shaped articulating bearing surface 33 is formed with compression mold 24, articulating bearing surface 33 is cooled and removed from within compression mold 24. A portion of articulating bearing surface 33 is machined using any suitable machining process to allow articulating bearing surface 33 to mate with an orthopaedic implant, such as tibial knee implant 42 shown in FIG. 3. For example, the portion of articulating bearing surface 33 on the bottom side of phantom line 44 (as viewed in FIG. 3) may be shaped and/or removed using a suitable machining process to allow articulating bearing surface 33 to mate with tibial knee implant 42. Of course, tibial knee implant 33 may be machined to define suitable keying and/or interlocking structures for interconnection with tibial knee implant 42.

In the embodiment shown, UHMWPE particles 12 are formed into articulating bearing surface 33 using compression mold 24. However, other suitable reforming methods may be used which apply heat and pressure, such as isostatic forming techniques, stamping, thermal forming, etc.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of manufacturing an articulating bearing surface for use in an orthopaedic implant, comprising the steps of:

providing a supply of ultra-high molecular weight polyethylene particles;

irradiating said particles with sufficient radiation energy to crosslink at least a portion of said ultra-high molecular weight polyethylene; and forming said irradiated particles into the articulating bearing surface.

2. The method of claim 1, wherein said forming step comprises the substeps of:

placing said irradiated particles into a mold;

pressing said irradiated particles within said mold; and heating said particles within said mold.

3. The method of claim 2, wherein said mold is heated above the melting point of said ultra-high molecular weight polyethylene.

4. The method of claim 2, wherein said mold comprises a compression mold.

5. The method of claim 1, wherein said particles comprise at least one of powder and flakes.

6. The method of claim 1, wherein said supply of particles comprises packets and said irradiating step comprises irradiating said particles within said packets.

7. The method of claim 6, wherein said supply of particles is formed by placing said packets of particles in a mold and pressing and heating the packet and particles within the mold.

8. The method of claim 1, wherein said irradiating step comprises irradiating said particles with sufficient radiation energy to crosslink substantially all of said ultra-high molecular weight polyethylene.

9. The method of claim 1, comprising the further step of reducing an amount of oxygen in an ambient atmosphere around said particles during said irradiating step.

10. The method of claim 9, wherein said step of reducing the amount of oxygen within said reforming apparatus comprises bathing said particles in an inert gas.

11. The method of claim 1, wherein said radiation energy consists of one of gamma rays, X-rays, ultraviolet radiation, neutron particle beam, proton particle beam and electron particle beam.

12. The method of claim 1, wherein said articulating bearing surface is configured for use with a tibial knee implant.

\* \* \* \* \*

UNITED STATES PATENT AND TRADEMARK OFFICE
CERTIFICATE OF CORRECTION

PATENT NO. : 6,143,232  
DATED : November 7, 2000  
INVENTOR(S) : William Rohr

Page 1 of 1

It is certified that error appears in the above-identified patent and that said Letters Patent is hereby corrected as shown below:

<u>Column 4,</u>  
Lines 52-54 should read as follow:  
10. The method of claim 9, wherein said step of reducing the amount of oxygen comprises bathing said particles in an inert gas.

Signed and Sealed this

Twenty-third Day of April, 2002

Attest:

Attesting Officer

JAMES E. ROGAN  
*Director of the United States Patent and Trademark Office*